United States Patent
Michelsson et al.

(10) Patent No.: US 7,477,370 B2
(45) Date of Patent: Jan. 13, 2009

(54) METHOD OF DETECTING INCOMPLETE EDGE BEAD REMOVAL FROM A DISK-LIKE OBJECT

(75) Inventors: Detlef Michelsson, Wetzlar-Naunheim (DE); Henning Backhauss, Wetzlar (DE); Gert Weniger, Jena (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 472 days.

(21) Appl. No.: 11/390,855

(22) Filed: Mar. 28, 2006

(65) Prior Publication Data

US 2007/0076194 A1     Apr. 5, 2007

(30) Foreign Application Priority Data

Mar. 31, 2005   (DE) ................ 10 2005 014 594

(51) Int. Cl.
  *G01N 21/00*   (2006.01)
  *G03B 27/32*   (2006.01)
(52) U.S. Cl. .................... 356/237.2; 355/77
(58) Field of Classification Search .......... 355/77; 356/237.2–237.6
  See application file for complete search history.

(56) References Cited

U.S. PATENT DOCUMENTS

| 7,180,585 B2 * | 2/2007 | Kreh et al. ............. 356/237.2 |
| 2004/0223141 A1 | 11/2004 | Rosengaus ............. 356/237.1 |
| 2004/0239920 A1 | 12/2004 | Kreh et al. ............. 356/237.3 |
| 2005/0013476 A1 | 1/2005 | Simpkins ................ 382/151 |
| 2005/0036671 A1 | 2/2005 | Watkins et al. .......... 382/145 |

FOREIGN PATENT DOCUMENTS

DE   103 24 474.3   12/2004

\* cited by examiner

*Primary Examiner*—Rodney E Fuller
(74) *Attorney, Agent, or Firm*—Simpson & Simpson, PLLC

(57) ABSTRACT

A method of detecting incomplete edge bead removal from a disk-like object is disclosed. First a peripheral area of a disk-like reference object is imaged. Marks are then defined in the peripheral area of the reference object. Finally, images of peripheral areas of a plurality of disk-like objects of the same batch are recorded. The inspection of the disk-like objects is limited to the locations of the marks defined on the reference object.

11 Claims, 5 Drawing Sheets

METHOD OF DETECTING INCOMPLETE EDGE BEAD REMOVAL FROM A DISK-LIKE OBJECT

CROSS REFERENCE TO RELATED APPLICATIONS

This patent application claims priority of German Patent Application No. 10 2005 014 594.9, filed on Mar. 31, 2005, which application is incorporated herein by reference.

FIELD OF THE INVENTION

The present invention relates to the detection of incomplete edge bead removal from a disk-like object.

BACKGROUND OF THE INVENTION

In semiconductor manufacture, during the manufacturing process, wafers (disk-like objects) are sequentially processed in a plurality of process steps, wherein a plurality of similar, repetitive structural elements, the so-called dies, are produced on a wafer.

In order to produce the dies, a plurality of photoresist layers must be applied one after the other on the wafer. During processing of the wafer, these applied photoresist layers are removed in a peripheral area. Checking the sufficient and complete removal of these photoresist layers is of considerable importance for the subsequent process steps. Remaining photoresist residues on the periphery of the disk-like object can lead to reduced quality when subsequent layers are applied and when the dies are structured.

The German Patent Application No. DE 103 24 474.3 A1 discloses an apparatus for wafer inspection. An incident-light lighting means having an illumination axis and an imaging means having an imaging axis are provided. The lighting means and the imaging means are inclined with respect to each other and directed towards the surface of a disk-like object. The quality of the peripheral area is determined by means of polarized light, and the image of the peripheral area is recorded by a linear array camera. Detecting complete edge bead removal, however, is not possible with the apparatus shown here.

US Patent Application US 2004/0223141 A1 discloses a detection of edge bead removal by means of reflection. A method and apparatus for improving the image contrast between an area covered with photoresist on the one hand and bare silicon on the other are disclosed. The method and apparatus can be used for inspecting the edge bead removal. Herein the wafer is illuminated separately with vertically polarized light and parallel polarized light in the vicinity of the Brooster angle of silicon or the photoresist. A difference image between the reflected, vertically polarized light and the reflected, parallel polarized light is generated. While the method or apparatus described here may be suitable for checking complete edge bead removal, the method or apparatus is based on a different technological principle from the present invention.

US Patent Application US 2005/0013476 A1 discloses a method of measuring the edge bead removal also comprising the detection of an edge at the circumference of the wafer. The position of the wafer notch at the periphery of the wafer is determined. The position of the wafer center is also determined. Moreover the distance between the wafer edge and the EBR (Edge Bead Removal) line is determined at the wafer circumference. The EBR line is determined from a bright field and a dark field.

From US Patent Application US 2005/0036671 A1, an apparatus for inspecting a periphery or edge of a wafer is known. The inspection device for semiconductor products comprises a camera for recording images of the peripheral area of the top surface of the wafer, a camera for imaging the circumferential surface, normal to the surface of the wafer, and a checking means for receiving the images of the peripheral area of the top surface of the wafer and from the circumferential surface of the wafer. The checking means is for analyzing the images of the peripheral area of the top surface of the wafer and of the circumferential surface of the wafer in order to be able to determine defects thereon.

SUMMARY OF THE INVENTION

It is therefore an object of the present invention to provide a method facilitating quick and reliable detection of incomplete edge bead removal with a plurality of wafers of a batch.

According to the present invention the present object is achieved by a method of detecting incomplete edge bead removal of a disk-like object, comprising the steps of:
- recording an image of a peripheral area of a disk-like reference object having its edge bead removed completely;
- showing the imaged peripheral area of the disk-like object on a display;
- marking at least one area, wherein the at least one area comprises structurable elements on the surface of the disk-like reference object;
- imaging one edge area of each one further disk-like object;
- applying marks on those areas of the imaged peripheral area of the further disk-like objects which correspond to the respective areas on the reference object; and,
- limiting the inspection with respect to the completeness of edge bead removal to the marked areas.

Therefore the present invention relates to a method of detecting incomplete edge bead removal of a disk-like object. The method is characterized by several steps. First, an image of a peripheral area of a disk-like reference object is taken, from which the edge bead has been completely removed. Then the imaged peripheral area of the disk-like object is shown on a display. The user marks at least one area, wherein the at least one area comprises structured elements of the surface of the disk-like reference object. Then one peripheral area of each further disk-like object is imaged. Usually, these are disk-like objects of the same batch. Finally, those areas of the imaged peripheral area of the further disk-like object which correspond to the respective areas of the reference object are provided with a mark. The inspection with respect to the completeness of the edge bead removal is limited to the marked areas. In the reference object, an edge bead removal line is also determined. Between this line and the edge of the disk-like object the photoresist must be completely removed. If during the inspection structured elements are found within the marked areas of the disk-like object to be inspected towards the edge of the disk-like object, a corresponding error message is issued indicating that the disk-like object currently inspected has an incompletely removed edge bead.

It is therefore sufficient for the inspection to be limited to the marked areas and for the presence of a photoresist removal edge to be looked for in the inspected areas.

If during the inspection no deviation is found between each marking of the disk-like object to be inspected and the reference object, a corresponding message is issued indicating that the edge bead removal is complete.

The peripheral area of the disk-like object is imaged by means of a linear array camera positioned above the surface of the disk-like object containing the peripheral area to be imaged. The peripheral area to be imaged is illuminated by a light source in a dark field array. This means that the structured elements present on a disk-like object are represented as dark areas in the recorded image of the disk-like object.

BRIEF DESCRIPTION OF THE DRAWINGS

Further advantages and advantageous embodiments of the invention are described in the following with reference to the accompanying drawings, in which.

DETAILED DESCRIPTION OF THE INVENTION

Figure 1:
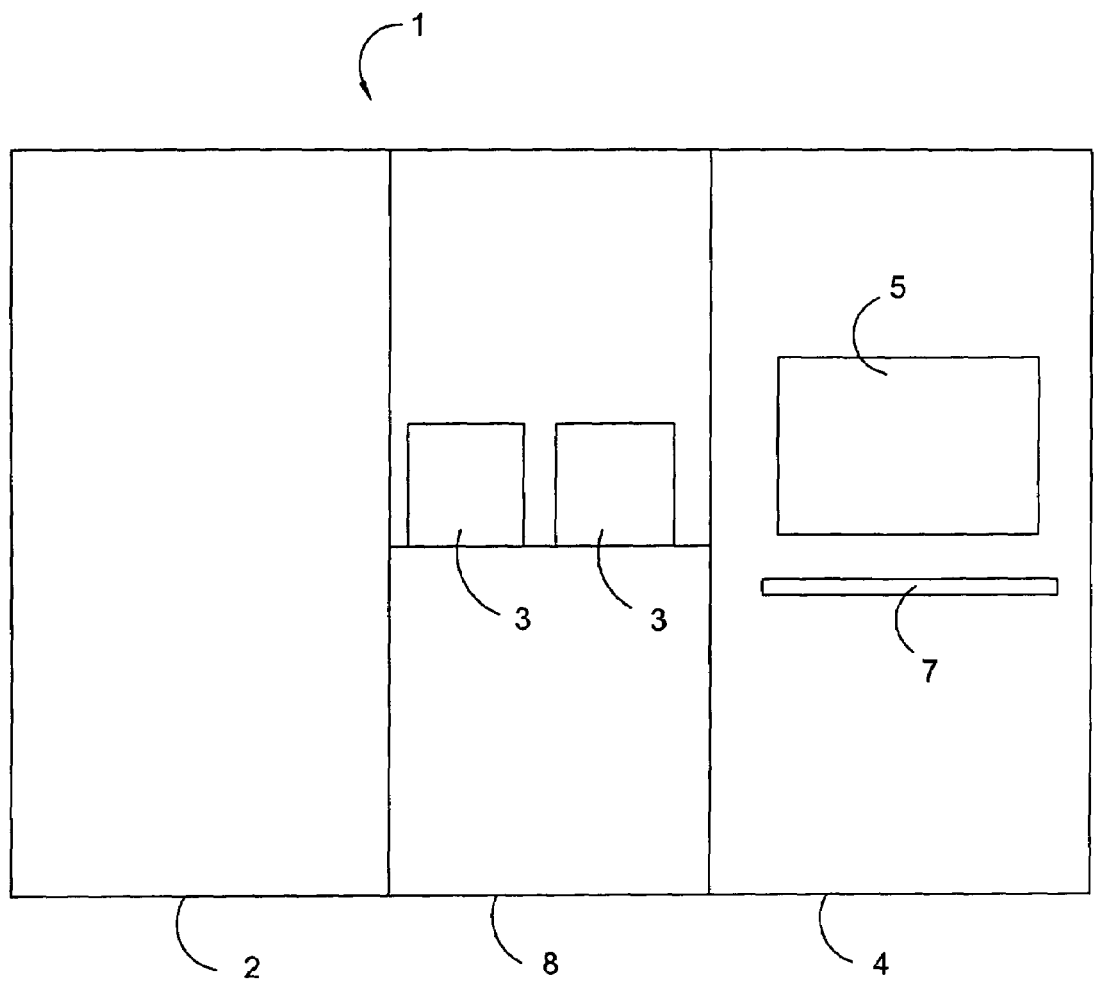
FIG. 1 is a schematic view of an apparatus for inspecting a disk-like substrate.

With reference to FIG. 1 an apparatus for inspecting a disk-like object or substrate is shown. Apparatus 1 for inspecting a disk-like substrate is comprised of a plurality of modules suitable for inspecting the disk-like object. In a first module 2, a macro inspection can be carried out. In a second module 4, subsequently, if necessary, a micro inspection of areas of interest on the disk-like object can be carried out. In the present embodiment a display 5 and an input unit 7 are provided on the second module allowing the user to enter respective specifications and parameters necessary for the inspection of the disk-like object. In the embodiment shown, the first module 2 and the second module 4 are connected via a third module 8. Containers 3 including the disk-like objects can be inserted on the third module 8 so that the disk-like objects can be introduced into apparatus 1 from the containers.

Figure 2:
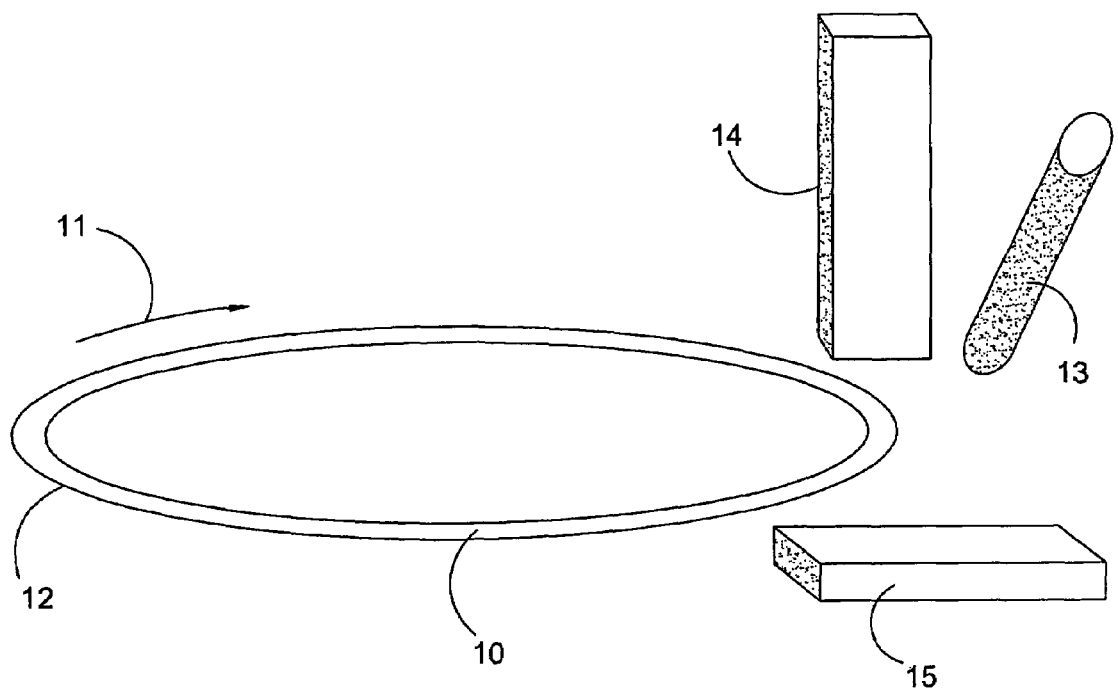
FIG. 2 is a schematic perspective view of an assembly for recording an image from a peripheral area of a disk-like object (wafer)

FIG. 2 is a perspective schematic view of the assembly for recording an image from a peripheral area 10 of a disk-like object 12. The disk-like object is rotated in the direction of arrow 11 as shown in FIG. 2. The rotation of the disk-like object 12 is effected by a rotary means not shown in the Figure. Facing the peripheral area 10 of the disk-like object 12, a camera 14 is provided for taking images of the peripheral area 10 of the disk-like object. The peripheral area 10 of the disk-like object 12 is imaged by having the disk-like object 12 rotate beneath camera 14. A light source 13 is associated with camera 14 or the disk-like object 12 in such a way that the peripheral area 10 of the disk-like object 12 is illuminated in a dark field. Also, another light source 15 is provided for illuminating the back of the disk-like object 12. This is to achieve a better contrast for identifying the periphery of the disk-like object.

Figure 3:
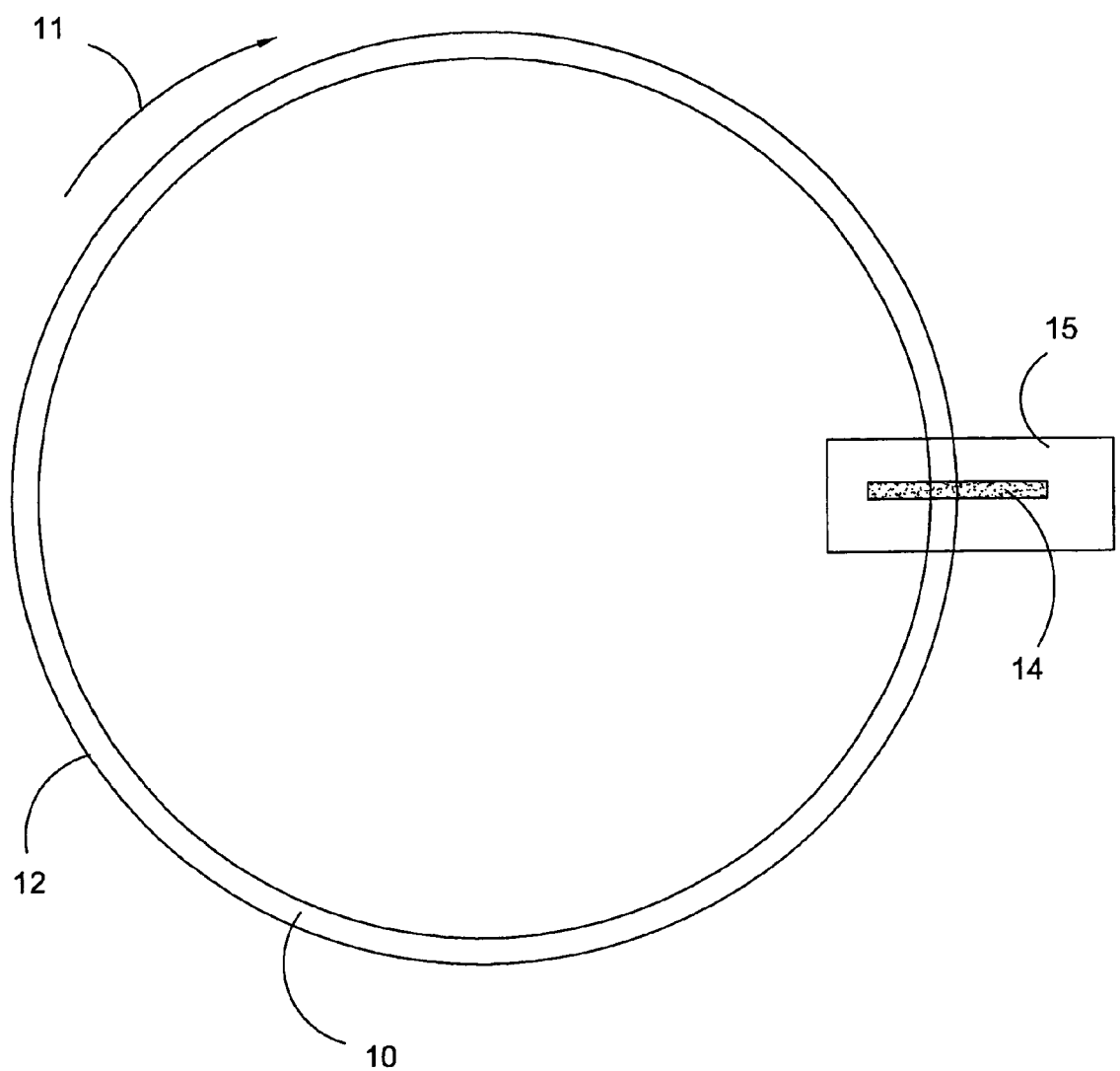
FIG. 3 is a top view of the assembly (FIG. 2) for recording an image of a peripheral area of a disk-like object (wafer)

FIG. 3 is a top view of the assembly shown in FIG. 2. As mentioned above, the disk-like object 12 is rotated in the direction of arrow 11. A camera 14 is associated with the disk-like object 12, which is configured as a linear array camera. Opposite linear array camera 14, there is a lighting means 15 for illuminating the back of the disk-like object 12 for better imaging the edge of the disk-like object 12. By rotating the disk-like object 12 beneath linear array camera 14, an image of the entire edge 10 of the disk-like object is recorded.

Figure 4:
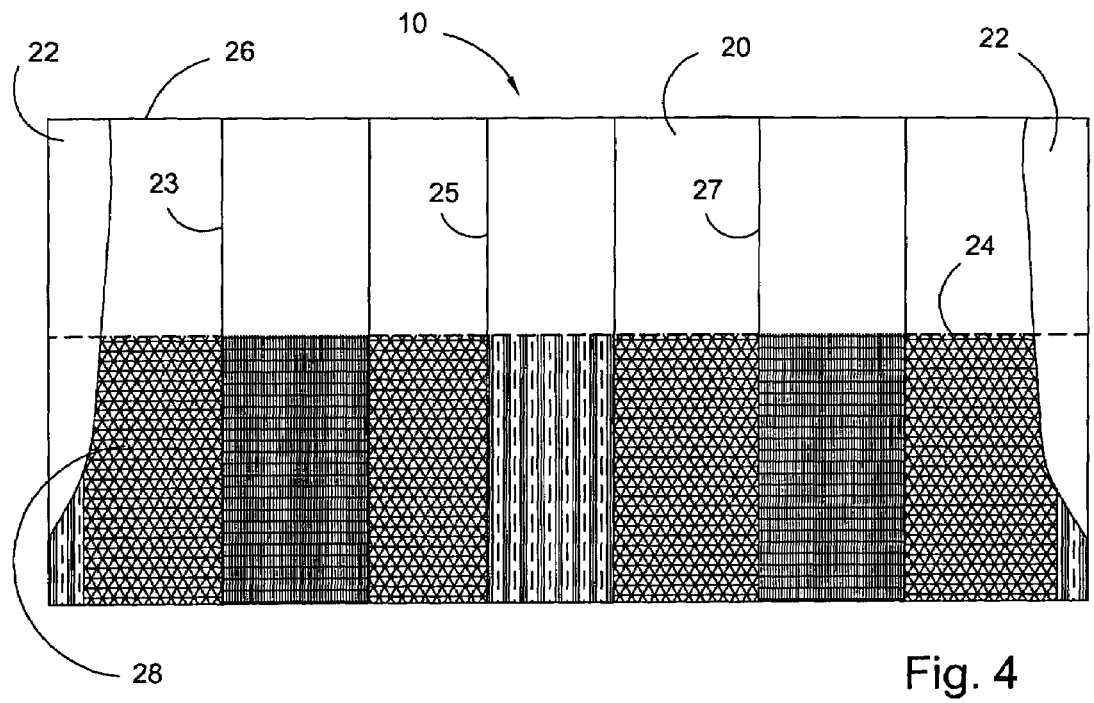
FIG. 4 is a schematic view of a recorded image from the peripheral area of a reference object.

FIG. 4 shows the recorded image of a peripheral area 10 of a disk-like object. The recorded peripheral area 10 of the disk-like object as shown in FIG. 4 serves as a reference. The image of peripheral area 10 shown in FIG. 4 is for training the system, which can then be used to detect photoresist residues on the wafer periphery. The training reference object therefore serves for comparison with other disk-like objects of the same batch. Image 20 of peripheral area 10 is shown to the user on display 5 as a rectangular development of the circular edge 10 of the disk-like object 12. At each right and left end of image 20, a notch or flat 22 of the wafer can be seen. The edge 26 of the disk-like object is also imaged by the linear array camera 14. The structured areas 28 of the disk-like object extend at a distance from the edge 26 of the disk-like object. Those skilled in the art will appreciate that the structured areas include the so-called dies of the disk-like object. The structured areas 28 and the unstructured areas of the disk-like object are separated by an EBR line 24. The user defines a plurality of marks 23, 25 and 27 in the reference image, wherein marks 23, 25 and 27 at least comprise structurable elements of the surface of the disk-like reference object. Marks 23, 25 and 27 are rectangular in shape and extend from structured area 28 to edge 26 of the disk-like object 12. This position of marks 23, 25 and 27 is based on the probability that structured elements on the surface of the disk-like object can extend beyond the EBR line 24 to the edge 26 of the disk-like object 12. The edge bead removal line 24 (also called an EBR line) determines that boundary beyond which after complete edge bead removal no photoresist residues may remain in the area between the EBR line 24 and the wafer edge.

Figure 5:
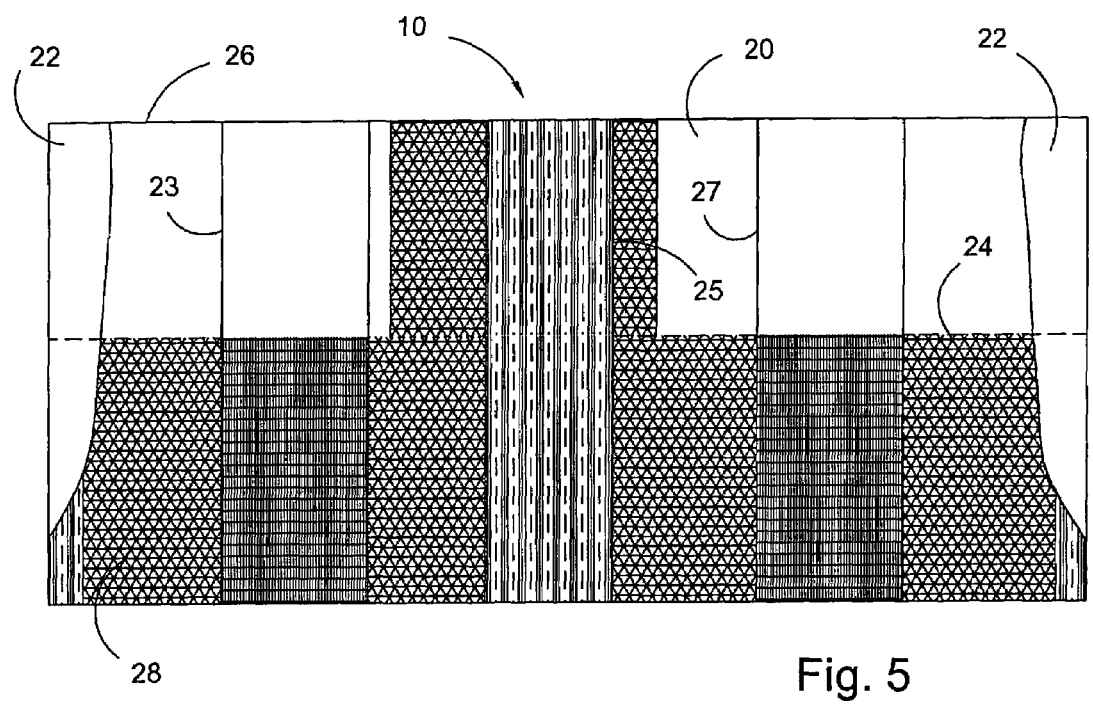
FIG. 5 is a schematic view of the recorded image from the peripheral area of a disk-like object, wherein the disk-like object is from the same batch as the reference object; and, FIG. 6 is a flow chart showing the sequence of steps of the method according to the present invention.

FIG. 5 is a schematic view 20 of the peripheral area 10 of a disk-like object of the batch which corresponds to the same process steps or type as the reference object of FIG. 4. The marks 23, 25 and 27 defined on the reference object remain in the same position for all disk-like objects of one batch. The system will only inspect the presence of structured elements or photoresist residues from the EBR line 24 to the edge 26 of the disk-like object. The limitation of the inspection to the marked areas 23, 25 and 27 has the considerable advantage that the inspection of the imaged edge of a disk-like object can be carried out much more quickly since the inspection is only limited to the marks 23, 25 and 27 defined on the reference object. In the example shown in FIG. 5, in the area of mark 25 a structure or photoresist residue extends up to the edge 26 of the disk-like object. As a consequence, no EBR line 24 can be found in the area of mark 25. This leads us to conclude that at least in one area of the wafer, the edge bead removal has not been carried out completely. Of course, a signal will be output to the user on display 5 or the like indicating that the process of photoresist removal is being or has been incompletely carried out. The method according to the present invention also has the advantage that if an EBR line is not found in a marked area 23, 25 or 27, the inspection of subsequent marks can be stopped. This means that considerable time can be saved in the inspection process.

Figure 6:
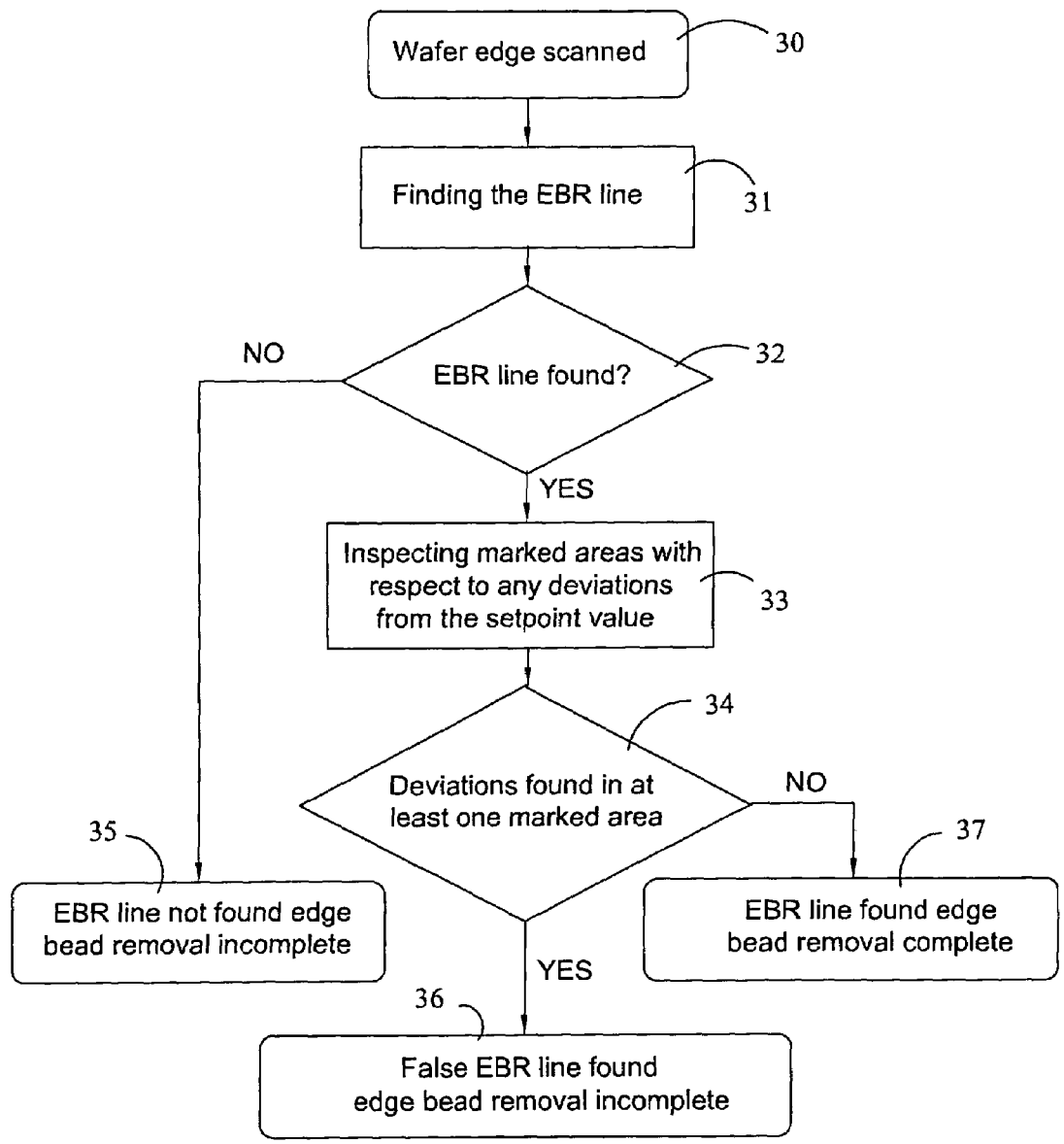

FIG. 6 schematically shows a flow chart of the method according to the present invention. The disk-like objects 12 are introduced into the system one after the other and their peripheral areas 10 are correspondingly imaged. The disk-like object 12 is usually a wafer so that the wafer edge is scanned or imaged in the apparatus. In a first step 30, the wafer edge is therefore scanned. In the recorded image, in a subsequent step 31, the EBR line is then searched for. In a decision step 32 it is asked whether or not the EBR line has been found. If the answer is "no", there is an output 35 indicating that there is no EBR line and edge bead removal is therefore incomplete. If "yes", it is checked whether in the marks there are any deviations from the reference object. The reference object (FIG. 4) is therefore a setpoint value, and any deviations from this setpoint value have to be identified as an error. In a further decision step it is asked whether or not any deviations have been found in at least one of the marks 23, 25 and 27 defined in the reference object. If the answer to the question in decision step 34 is "yes", another message 36 is issued indicating that the EBR line found cannot be a photoresist edge since there are photoresist structures extending beyond this line and that therefore the edge bead removal is incomplete in at least one area of the disk-like object. If, however, no deviation with respect to the reference object is found, an output 37 is issued indicating that the EBR line has been found and that the edge bead removal up to edge 26 of the disk-like object is complete.

What is claimed is:

1. A method of detecting incomplete edge bead removal of a disk-like object, comprising the steps of:
    recording an image of a peripheral area of a disk-like reference object having its edge bead removed completely;
    showing the imaged peripheral area of the disk-like object on a display;
    marking at least one area, wherein the at least one area comprises structurable elements on the surface of the disk-like reference object;
    imaging one edge area of each one further disk-like object;
    applying marks on those areas of the imaged peripheral area of the further disk-like objects which correspond to the respective areas on the reference object; and,
    limiting the inspection with respect to the completeness of edge bead removal to the marked areas.

2. The method according to claim 1, wherein an EBR line is determined from which a complete edge bead removal toward the edge of the disk-like object is to be carried out.

3. The method according to claim 1, wherein the inspection is limited to only the marked areas.

4. The method according to claim 1, wherein all disk-like objects of a batch are inspected with the aid of the marks obtained from the reference object.

5. The method according to claim 1, wherein the EBR line is looked for and a message is issued if an EBR line is not found.

6. The method according to claim 1, wherein within each mark, a deviation from the reference object is looked for and wherein, if there is a deviation, a message is issued indicating that the edge bead removal is incomplete.

7. The method according to claim 6, wherein when it is determined that there are no deviations between each mark and the reference object, a message is issued indicating that the edge bead removal is complete.

8. The method according to claim 1, wherein the peripheral area of the disk-like object is imaged with a linear array camera arranged above the surface of the disk-like object comprising the peripheral area to be imaged.

9. The method according to claim 8, wherein the peripheral area to be imaged is illuminated by a light source in a darkfield array.

10. The method according to claim 8, wherein the peripheral area of the surface of the disk-like object which faces away from the linear array camera is illuminated by a light source with incident light.

11. The method according to claim 1, wherein the disk-like object is a wafer on which the required structures have been formed.

* * * * *